United States Patent [19]
Elmer et al.

[11] Patent Number: 5,159,129
[45] Date of Patent: Oct. 27, 1992

[54] $H_2O$ ADDITION IN ACID CATALYZED PROCESSING

[75] Inventors: Gary W. Elmer, Dickinson; William D. Meyer, Friendswood; Cedric A. Pereira, Houston; Robert W. Puschinsky, Seabrook, all of Tex.

[73] Assignee: Amoco Corporation, Chicago, Ill.

[21] Appl. No.: 616,404

[22] Filed: Nov. 21, 1990

[51] Int. Cl.$^5$ .............................. C07C 2/56; C07C 2/58
[52] U.S. Cl. ................................... 585/717; 585/721; 585/724
[58] Field of Search .................. 585/717, 721, 724

[56] References Cited
U.S. PATENT DOCUMENTS 2,431,685  12/1947  Cade .................................. 585/724
3,778,489  12/1973  Parker et al. ....................... 585/724
4,918,255   4/1990  Chou et al. ......................... 585/721
4,950,824   8/1990  Shiroto et al. ..................... 585/320

Primary Examiner—Asok Pal
Assistant Examiner—Nhat Phan
Attorney, Agent, or Firm—William H. Magidson; Frank J. Sroka; Robert J. Wagner

[57] ABSTRACT

A process and apparatus for the addition of $H_2O$ in acid catalyzed processing of hydrocarbons are disclosed. The $H_2O$ is added to the hydrocarbons in the form of steam, increasing the quantity of $H_2O$ dissolved in the acid catalyst after contact of the acid catalyst with the steam-added hydrocarbon feed. Entrained water present in the steam-added hydrocarbon feed can be decanted prior to contacting the acid with the feed.

18 Claims, 1 Drawing Sheet

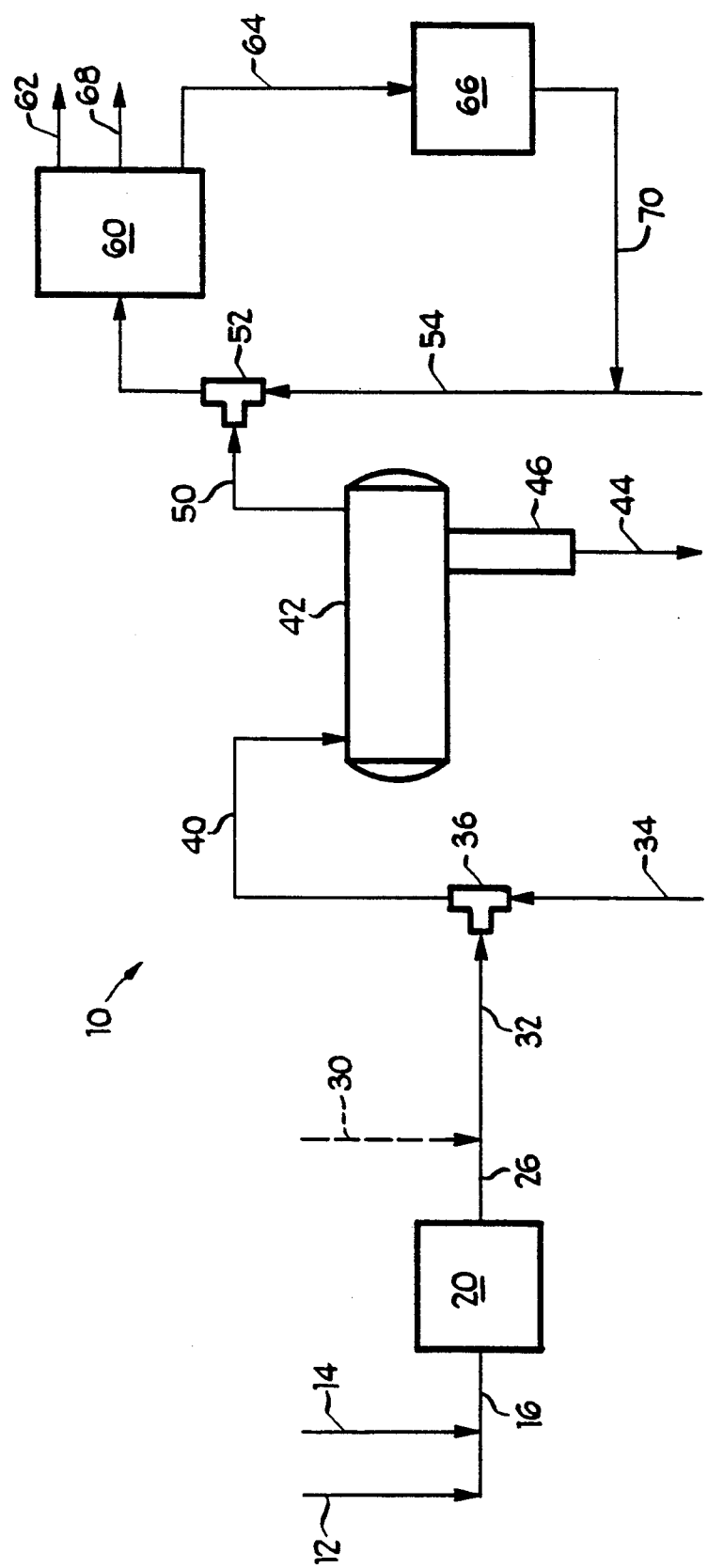

H₂O ADDITION IN ACID CATALYZED PROCESSING

BACKGROUND OF THE INVENTION

This invention relates generally to acid catalyzed processing of hydrocarbons and, more specifically, to increasing the dissolved H$_2$O content in such processing.

A wide variety of reactions are catalyzed or otherwise promoted by substances generally classified as acids. The alkylation of isoparaffins with olefins is one such reaction.

High octane material can be produced by reacting an isoparaffin such as isobutane with $C_2$-$C_5$ olefins, forming branched chain isoparaffinic hydrocarbons in the gasoline boiling range. Such processing is commonly referred to as alkylation. Alkylation can be done under both thermal and catalytic conditions. Thermal alkylation typically requires high temperatures (about 500° C. or more) and pressures (about 150 to 300 atm). Catalytic alkylation, in contrast, generally occurs at significantly lower temperatures and pressures. While dependent on the catalyst used in such processing, the temperatures used are usually in the range of from about −30° to about 100° C. and the pressure need only be sufficient to maintain the reactants in the liquid phase.

The catalytic alkylation of an isoparaffin with one or more olefins to produce a branched chain paraffin, using hydrofluoric acid (HF) as a catalyst, is a commercially important process for producing high octane gasoline.

Depending on the olefin used in alkylation, the alkylate octanes are usually 90 to 96 RON (Research Octane Number) and 88 to 94 MON (Motor Octane Number). The production of high, clear octane makes alkylate a desirable feedstock for gasolines. In addition, alkylate is typically nontoxic, has a high heat of combustion, and is good for both high and low-speed driving.

Butylenes are a preferred alkylation olefinic feed because they typically produce the highest octane alkylate at the least cost with common catalyst. Propylene and amylenes (pentenes) can also be readily alkylated. Ethylene is rarely alkylated. Alkylation feed is typically charged directly from a catalytic cracking and/or a coking unit. Additional isobutane, other than the amount present in these olefinic feeds, is commonly required for the alkylation process. Sources for such additional isobutane may include the crude unit, reformer, hydrocracker, isomerate and purchased field butanes, for example.

Products of the process may typically include alkylate, LPG (Liquified Petroleum Gas) and normal butane. Existing and potential environmental/health regulations limiting lead, olefins and/or aromatics in gasoline may, in the future, increase the need for alkylation to maintain refinery pool octanes.

Catalytic alkylation processing was first commercialized using a sulfuric acid catalyst. This was followed shortly thereafter by the first alkylation unit to use hydrofluoric acid (HF) as an acid catalyst for alkylation.

In general, in alkylation processes, an alkylatable material, e.g., an isoparaffin, preferably isobutane, for example, is reacted with an alkylating agent, e.g., an olefin, preferably a light olefin such as propylene, butylenes or amylenes. The feed typically consists of several olefins and paraffins, while the alkylate product contains numerous compounds in the $C_5$ to $C_{12}$ range. All true reaction products are at least singly branched. (Note: Some feed components are unbranched, nonreactive n-paraffins which become part of the alkylate. Hydrogen-transfer reactions also produce normal paraffins.) Normal paraffins are typically also present in the feed and generally cannot be economically eliminated prior to reaction. For the most part, however, such normal paraffins are unaffected in the process.

Two liquid phases typically exist in the alkylation reactor because alkylate and the isoparaffin, e.g., isobutane, are only sparingly soluble in the acid phase. However, the alkylation reaction is thought to generally occur in the acid phase.

In addition, while isobutane is only slightly soluble in the acid (about 3% in hydrofluoric acid), the olefins are essentially infinitively soluble in the acid in the form of an ester. Therefore, high isobutane to olefin ratios must be used to assure that the alkylation rather than polymerization reactions occur. High mixing intensities are also required so that the isobutane lost by reaction from the acid phase can be replenished and olefins will be widely dispersed to minimize polymerization.

While commercial isoparaffin-olefin alkylation is normally catalyzed by sulfuric or hydrofluoric acid, neither of these acid catalysts can conveniently be used to alkylate ethylene, because, in such processing, ethylene merely forms stable esters.

Hydrofluoric acid alkylation generally occurs at about 75° to about 100° F. in commercial units, while the sulfuric acid process typically operates at about 30° to about 65° F. Hydrofluoric acid can perform well at a higher temperature because of its greater isobutane solubility. This property in combination with the much lower density of hydrofluoric acid as compared to sulfuric acid, allows hydrofluoric acid systems to typically operate without requiring the use of reactor mixers. In addition, hydroflouric acid unit reactor temperatures can generally be maintained by using normally available cooling water and controlling olefin flow rate. In contrast, the sulfuric acid-catalyzed process temperature is limited by increased acid viscosity and possible acid freezing at the lower bound and acid degeneration due to oxidation at the upper bound. Thus, using a hydrofluoric acid as opposed to a sulfuric acid catalyst process can save refrigeration system costs.

In such alkylation processing, although the acid is a catalyst, it is "used" by reaction with contaminants and diluted with polymerization products. Because acidity must be maintained above a minimum strength to avoid rapid acidity decay (due to polymerization being increasingly favored over alkylation as acidity declines), fresh acid typically must periodically be added in the process.

Wet HF acid, however, can be extremely corrosive and consequently feed streams in HF alkylation units are typically dried prior to use. Standard HF alkylation unit designs include wet feed stream driers (commonly designed to result in the stream passing therethrough to exist containing no more than about 20–50 ppm of water therein) to guard against high water concentrations and the presence of entrained or "free" water, which can contribute to increased corrosion and acid consumption. For example, treatment of the specified stream with bauxite or molecular sieves is commonly used for such drying. Water leakage past the driers, however, concentrates in the acid and is subsequently removed from the process system along with the acid soluble oil (ASO), via the acid rerun tower bottoms. The amount of feedstock impurities will typically govern the frequency and severity of acid rerun tower operation and hence the equilibrium water content of the HF acid. Thus, when using a relatively poor quality of fresh hydrocarbon feed, the $H_2O$ content of the acid will, over time, be significantly reduced.

The presence of a moderate level of water in the acid phase, however, has been reported to have a beneficial effect on the alkylate composition produced in hydrofluoric acid units. Hutson and Hays of Phillips Petroleum Company, in "Reaction Mechanism for Hydrofluoric Acid Alkylation," ACS Symp. Ser., 55 (Ind. Lab, Alkylations), pp. 27–56 (1977), have shown that increasing the water in acid from 0.25% to about 2.8% decreases the formation of low octane $C_9+$ material. The authors have also identified that proper water control may be significant in order to maximize alkylate quality and yield.

In view of the beneficial octane effects achieved through maintaining the $H_2O$ content of the acid within a specified range and the known corrosive effects of undesirably high water concentrations and the presence of entrained water in HF acid, a process and a system for the safe addition of $H_2O$ is needed.

Over the years various processes and equipment have been suggested in patents for catalytic alkylation using HF acid catalyst. Included in these patents are U.S. Pat. Nos. 4,276,439 and 4,383,977 which disclose that the hydrogen fluoride catalyst is generally 85 to 98 wt. % HF and 2 to 15 wt. % water, acid soluble oils and hydrocarbons; U.S. Pat. Nos. 4,220,806 and 4,225,737 which disclose that the alkylation catalyst employed therein generally contains about 75 wt. % or more of titratable acid, about 5 wt. % or less of water and the remainder constituting organic diluent, with a particular preferred catalyst comprising about 85 wt. % hydrofluoric acid and less than about 1 wt. % water; U.S. Pat. No. 4,214,114 which discloses that it is possible to use hydrofluoric acid containing as much as about 10% water; U.S. Pat. No. 4,207,423 which discloses that the water content of the catalyst phase should be between about 0.5 and 5.0 wt. %, preferably below about 2 wt. % of the total catalyst phase and still more preferably below about 1.5 wt. % of the total catalyst phase; U.S. Pat. No. 3,726,940 which identifies 2 wt. % water as the optimum water concentration of the fluid stream flowing to the conduit into the rerun column; and U.S. Pat. No. 2,570,574 which identifies that the hydrogen fluoride catalyst may contain minor quantities (up to 5%–10%) of water although substantially anhydrous hydrogen fluoride is preferred.

None of these patents show or suggest a process or system for a safe addition of $H_2O$ to an HF alkylation system.

SUMMARY OF THE INVENTION

It is an object of the present invention to overcome one or more of the problems described above.

According to the invention, a system for the safe addition of $H_2O$ to a non-hydrocarbon acid-catalyzed reaction system wherein hydrocarbons are contacted with acid catalyst is provided. The system includes means for adding steam to the hydrocarbon feed to the reaction system. The steam addition serves to increase the quantity of $H_2O$ dissolved in the acid catalyst after contact of the acid catalyst with steam-added hydrocarbon feed. The system also includes, prior to the point of contacting the non-hydrocarbon acid with the steam-added hydrocarbon feed, means for decanting entrained water from the hydrocarbon feed to which the steam has been added.

In one embodiment of the invention, a system is provided for the addition of $H_2O$ to an HF alkylation unit wherein a hydrocarbon feed comprising an alkylatable material and an alkylating agent are contacted with hydrofluoric acid to produce a high octane alkylate product. Absent such $H_2O$ addition, the hydrofluoric acid, after contact with hydrocarbon feed, has a dissolved $H_2O$ content of less than about 1.5 wt. %, based on the combined weight of $H_2O$ and hydrofluoric acid. The system includes means for adding substantially dry steam to the alkylatable material, the alkylating agent, or both, to increase the dissolved $H_2O$ content of the hydrofluoric acid, after contact with the steam-added hydrocarbon feed, to no more than about 5 wt. %. The system also includes means for mixing the added steam with the alkylatable material the alkylating agent, or both, to which the steam has been added to more uniformly distribute the steam therein. In addition, the system includes means for decanting entrained water from the steam-added hydrocarbon feed prior to contacting the steam-added hydrocarbon feed with the hydrofluoric acid.

In another embodiment of the invention, a method for adding $H_2O$ to a non-hydrocarbon acid-catalyzed reaction system for the catalytic reaction of hydrocarbon is provided. The method includes admixing steam with the hydrocarbon feed to increase the dissolved $H_2O$ content of the acid after contact with the steam-added hydrocarbon feed, with the combined acid and hydrocarbon feed being substantially free of entrained water.

An alternative embodiment of the invention provides a method for the alkylation of a hydrocarbon feed of an alkylatable material and an alkylating agent, in the presence of hydrofluoric acid. The method includes contacting the alkylatable material with the alkylating agent, in the presence of hydrofluoric acid with at least either the alkylatable material or the alkylating agent having had sufficient substantially dry steam admixed therewith to increase the dissolved $H_2O$ content of the acid, after contact with the steamadded hydrocarbon feed to no more than about 5 wt. %. Absent such addition of $H_2O$, the hydrofluoric acid, after contact with hydrocarbon feed, would have a dissolved $H_2O$ content of less than about 1.5 wt. %. The contacting is at a temperature and pressure and for a contact time sufficient to alkylate the alkylatable material to produce high octane alkylate product.

In an additional embodiment of the invention, the alkylatable material includes the isoparaffin isobutane and the alkylating agent includes at least one light olefin. The alkylatable material and the alkylating agent are contacted in the presence of hydrofluoric acid at HF alkylation conditions including temperature, pressure and contact time sufficient to alkylate the isoparaffin to produce a high octane alkylate product. The method of alkylation includes the step of admixing sufficient superheated steam with the hydrocarbon feed to increase the dissolved $H_2O$ content in the hydrofluoric acid after contacting the hydrofluoric acid with the steam-admixed hydrocarbon feed to no more than about 2 to 3 wt. %, followed by decanting entrained water from the steam-admixed hydrocarbon feed when entrained water is present therein. This results in the feed being substantially free of entrained water on contact with the hydrofluoric acid.

The term "substantially dry" as used herein in reference to added steam means that the steam is free of any significant content of entrained or "free" water which may detrimentally affect acid catalyst activity or increase corrosion. In practice, such "substantially dry steam" will generally be at least about 95% and preferably more than about 99% free of such entrained water, that is, at least about 95% and preferably more than about 99% of any such entrained water in the stream will have been removed.

Other objects and advantages of the invention will be apparent to those skilled in the art from the following detailed description taken in conjunction with the appended claims and drawing.

BRIEF DESCRIPTION OF THE DRAWING

The FIGURE is a simplified schematic flow diagram for the addition of $H_2O$ to an HF alkylation unit in accordance with a preferred embodiment of the invention.

DETAILED DESCRIPTION OF THE INVENTION

The present invention provides a process and system for the safe addition of $H_2O$ in acid-catalyzed processing, specifically non-hydrocarbon acid-catalyzed processing.

While the process and system of the invention are described hereinafter with particular reference to the hydrofluoric acid (HF)-catalyzed alkylation of a hydrocarbon feed, it will be apparent that the processing system also has application to other HF catalyzed processes of hydrocarbon feeds, as well as other acid catalyzed alkylation processes, and other acid-catalyzed processes of hydrocarbon feed, particularly non-hydrocarbon acid-catalyzed processes, such as polymerization, with the catalyst of phosphoric acid on kieselguhr, for example.

Referring to the Figure, a simplified, partial schematic flow diagram, generally designated by the numeral 10, of a system for the safe addition of $H_2O$ to an HF alkylation unit is shown. In the system 10 an alkylatable material feed stream 12 and an alkylating agent feed stream 14 are added together to form a combined feed stream 16. The combined feed stream 16 is passed to a drier unit section 20. The drier unit section serves to dry the combined feed stream so that the dried combined feed stream 26 exiting from the drier unit section contains no more than about 20 to 50 ppm $H_2O$. Such drying or water removal helps ensure that no feed containing an unacceptable amount of moisture is passed to the acid-catalyzed reactor. Such drying or water removal can be effected through common or known water removal techniques such as through the use of a drier packed with an absorbant material such as alumina or a molecular sieve having a high affinity for water, for example.

Of course, depending on the water content of the material, at least some and, if desired, all feed stream material may bypass the feed driers. For example, as shown in phantom, a feed stream 30 of material already sufficiently dry is added to the dried combined feed stream 26 to form the feed stream 32.

Steam, such as from the stream 34, is then added to the dry hydrocarbon feed 32. The steam addition can be accomplished through the use of an injector or the like or, as shown in the Figure for a preferred embodiment of the invention, through a mixing tee 36 whereby desired mixing of the added steam to the dry hydrocarbon feed can be realized.

To minimize water condensation upon contacting the added steam with the dry and relatively cooler hydrocarbon feed, the steam utilized in the practice of the invention is preferably a substantially dry steam, preferably a superheated steam. Such superheated steam should preferably contain at least about 25° F. of superheat and, more preferably, at least about 100° F. of superheat.

The combined hydrocarbon feed plus steam forms a stream 40 which is passed to a coalescer 42. In general, a coalescer is a vessel that contains a material, such as a pad of woven glass or other fibers, to capture entrained water. On the passage of a stream containing entrained water through the coalescer, the fibers or other "capturing" material becomes wetted by the water, capturing small droplets of such water. The small captured droplets of water are then coalesced into large droplets of water. As the large droplets of water form they fall and collect in the boot portion of the coalescer. The coalescer will preferably be operated in a fashion whereby accumulated water is at least periodically and, if needed or preferred, continuously drawn off to avoid the carrying over of free water with the hydrocarbon feed. For example, as a precaution to avoid risking such carrying over of free water, the coalescer and system can be controlled to discontinue $H_2O$ addition to the process system whenever the water level in the boot rises to more than 30% of capacity.

In the coalescer 42 entrained water is removed through a water draw stream 44 off of the boot 46 of the coalescer 42. In this fashion, substantially all water which may be present in the stream 40 as a separate phase is removed.

A stream 50 of steam-admixed hydrocarbon feed exits the coalescer 42 and is mixed, such as in a mixing tee 52, with hydrofluoric acid, such as from a stream 54 to form a combined total feed stream 56. The total combined feed stream is fed to a reactor 50 wherein the desired alkylation is completed, forming a alkylate product stream 62.

A stream 64 containing diluted, used hydrofluoric acid is preferably treated such as through "regeneration," such as in a rerun column 66, to form hydrofluoric acid in the desired strength or concentration (shown as stream 70) and preferably is recycled in the process.

In addition, if desired, unreacted hydrocarbons from the reactor 60, shown as a stream 68, may and preferably are recycled in the process.

As discussed above, a preferred alkylatable material for use in the process of the invention is the isoparaffin, isobutane. The alkylating agent is preferably a light olefin, e.g., a $C_3$-$C_5$ olefin or a mixture of one or more of these. It is to be understood, however, that the hydrocarbon feed will, as described above, typically contain at least some normal paraffin materials. For example, a typical alkylating agent feedstock to an HF alkylation unit may include a propane-propylene stream (typically from about 55 to about 70 wt. % propylene) and a butane-butylene stream (typically from about 40 to about 65 wt. % butylene). In addition, one or more of such alkylating agent feedstock streams may contain significant amounts of $C_5$ olefins (amylenes). For example, a butane-butylene stream may contain up to about 2 to 15 wt. % C$_5$ olefins.

In practice, the amount of H$_2$O addition to the hydrocarbon feed, at a given pressure, can be, and preferably is, limited by the solubility of H$_2$O in the hydrocarbon feed at the selected temperature of the coalescer (or other decanting means). Thus, the extent or amount of H$_2$O added is relatively accurately controlled by means of controlling or regulating the temperature of the coalescer (or other decanting means).

Generally, water solubility in the hydrocarbon stream is a function of temperature, pressure, and composition of the hydrocarbon stream. In practice, the pressure is maintained at a fairly constant level and the composition of the hydrocarbon stream is not varied to any significant extent to affect the water solubility in the stream. Consequently, in such circumstances, H$_2$O addition can be relatively easily and safely governed by controlling the temperature of the coalescer (or other decanting means, for example) to a selected maximum temperature or limited operating temperature range.

Hydrocarbon feed temperatures, prior to the addition of steam, typically range from about 80° to about 90° F. The addition of steam, as described above, and in accordance with the invention, will typically result in the temperature of such hydrocarbon feed increasing to no more than about 130° F. and generally to about 100° to about 110° F.

The invention provides a technique for adding H$_2$O to an acid-catalyzed reaction system so as to relatively safely increase the dissolved H$_2$O content of the acid. In general, the practice of the invention wherein steam is added to the alkylatable material, the alkylating agent, or both, of the hydrocarbon feed of the HF alkylation unit will find particular utility with such processing wherein the hydrofluoric acid has a dissolved H$_2$O content of less than about 1.5 wt. %, based on the combined weight of H$_2$O and hydrofluoric acid. In the practice of the invention, it is preferred that the dissolved H$_2$O content of the hydrofluoric acid be increased by way of the steam-added hydrocarbon feed to no more than about 5 wt. % and, more preferably, to a range of no more than about 2 to 3 wt. %, based on the combined weight of H$_2$O and hydrofluoric acid.

It is to be understood that while the invention has been described above with the use of a mixing tee to promote mixing, other steam addition and/or mixing means and techniques can be used in place of or as a supplement to a mixing tee. For example, other addition and/or mixing means such as in line static mixers, valve(s) and orifice(s) can, if desired, be used, as appropriae, for desired addition and mixing.

Also while the invention has been described above with the use of a coalescer to effect separation and removal of entrained or free water from the steam-added hydrocarbon feed prior to contacting the steam-added hydrocarbon feed with the hydrofluoric acid catalyst, it is to be understood that other means of decanting entrained water can be used in the practice of the invention, if desired. Such other decanting means include decanters, settling drums and some electrostatic devices like desalters, for example.

The following examples illustrate the benefits and various aspects of the practice of the invention. It is to be understood that all changes and modifications that come within the spirit of the invention are desired to be protected and thus the invention is not to be construed as limited by these examples.

EXAMPLES

A process system similar to that shown in the FIGURE was operated both without H$_2$O addition and with H$_2$O addition, in accordance with the invention. A total of 85 Runs were made, 49 of these Runs were done without water addition, while 36 of the Runs were done with H$_2$O addition as described above.

Table 1 shows and confirms the effect of water content on both research and motor octane numbers.

TABLE 1

| Increase in water-in acid (wt. %) | | | | |
|---|---|---|---|---|
| From | To | RON | MON | (R + M)/2 |
| 0 | 1 | +0.9 | +0.8 | +0.85 |
| 1 | 2 | +0.7 | +0.2 | +0.45 |
| 2 | 3 | +0.3 | +0.1 | +0.20 |

Both the research and motor octane numbers shown above have been adjusted to a "true C$_{5+}$ alkylate basis" that is, the alkylate octane has been adjusted by subtracting the octane contribution of any butanes in the alkylate product stream and adjusting the octane contribution of pentanes to include only the net contributions of pentanes produced in the alkylation unit. The water concentration in acid was measured by the Karl Fischer test.

In a process system similar to that shown in the FIGURE, a dry hydrocarbon feed stream (stream "32"), at 85° F. and 155 psig, was admixed with sufficient specified superheated steam (stream "34") to raise the temperature of the combined hydrocarbon and steam stream (stream "40") to 119° F., which was passed to a coalescer ("42"). In the coalescer, liquid water condensate (stream "44") was removed, resulting in a stream-admixed hydrocarbon feed stream (stream "50"). The operating conditions, as well as flow rates and conditions of the relevant streams are identified below.

---

STREAM "32"
  15,565 lbs/hr propane-propylene
  178,399 lbs/hr isobutane
  32,953 lbs/hr normal C$_4$
  98,667 lbs/hr butylenes
  38,971 lbs/hr total C$_5$
  12 lbs/hr H$_2$O
  364,567 lbs/hr TOTAL (85° F., 155 psig)

STREAM "34"
  6085 lbs/hr H$_2$O (600° F., 400 psig)

COALESCER "42"
  119° F., 150 psig

STREAM "44"
  5908 lbs/hr H$_2$O

STREAM "50"
  15,565 lbs/hr propane-propylene
  178,399 lbs/hr isobutane
  32,953 lbs/hr normal C$_4$
  98,667 lbs/hr butylenes
  38,971 lbs/hr total C$_5$
  189 lbs/hr H$_2$O
  364,744 lbs/hr TOTAL
  (119°, 150 psig, ~500 ppm H$_2$O)

---

The solubility of water in the hydrocarbon stream at 119° F. (the temperature of the coalescer at the operating pressure of 150 psig) safely limits and controls the water content in the hydrocarbon, for subsequent contact with HF acid catalyst, to only about 500 ppm H$_2$O. In contrast, if instead of the above-described processing, liquid water was added at 85° F., the maximum content of dissolved water in the hydrocarbon effluent leaving the coalescer (operating at 85° F.) would be limited to only about 230 ppm $H_2O$.

From the foregoing description, one skilled in the art can easily ascertain the essential characteristics of this invention and, without departing from the spirit and scope thereof, can make various changes and modifications of the invention to adapt it to various usages and conditions.

That which is claimed is:

1. A method for adding $H_2O$ to a reaction system for the catalytic reaction of a feed comprising hydrocarbons, said catalytic reaction system utilizing a liquid non-hydrocarbon acid catalyst having a dissolved liquid $H_2O$ content, said method comprising admixing steam with the hydrocarbon feed to increase the dissolved $H_2O$ content of the non-hydrocarbon acid after contact with the steam-added hydrocarbon feed, as compared to the liquid non-hydrocarbon acid catalyst prior to contacting with the steam-added hydrocarbon feed, and wherein the combined acid and steam-added hydrocarbon feed are substantially free of entrained water.

2. The method of claim 1 wherein said admixed steam is substantially dry.

3. The method of claim 2 wherein said substantially dry steam is superheated and comprises at least about 25° F. of superheat.

4. The method of claim 1 wherein said steam-added hydrocarbon feed comprises entrained water, said method additionally comprising the step of decanting entrained water from said steam-added hydrocarbon feed prior to contacting the steam-added hydrocarbon feed with acid catalyst.

5. The method of claim 1 wherein said catalytic reaction of hydrocarbons is catalytic alkylation.

6. The method of claim 5 wherein the non-hydrocarbon acid catalyst is hydrofluoric acid.

7. The method of claim 6 wherein, absent such $H_2O$ addition, the hydrofluoric acid after contact with hydrocarbon feed, has a dissolved $H_2O$ content of less than about 1.5 wt. %, based on the combined weight of $H_2O$ and hydrofluoric acid, and, with said $H_2O$ addition, the temperature of said hydrocarbon feed is increased and the hydrofluoric acid, after contact with the steam-added hydrocarbon feed, has a dissolved $H_2O$ content increased to no more than about 5 wt. %.

8. The method of claim 7 wherein said admixing of steam increases said dissolved $H_2O$ content to about 2 to 3 wt. %.

9. The method of claim 6 wherein, absent said admixing of steam, the temperature of said hydrocarbon feed is about 80° to about 90° F., and, with said admixing of steam, the temperature of the steam-added hydrocarbon feed is increased to no more than about 130° F.

10. The method of claim 9 wherein the temperature of said steam-added hydrocarbon feed is increased to a range of about 100° to 110° F.

11. A method for the alkylation of a hydrocarbon feed, comprising an alkylatable material and an alkylating agent, in the presence of hydrofluoric acid, said method involving addition of $H_2O$ wherein, absent the addition of $H_2O$, the hydrofluoric acid, after contact with hydrocarbon feed, has a dissolved liquid $H_2O$ content of less than about 1.5 wt. %, based on the combined weight of $H_2O$ and hydrofluoric acid, said method comprising contacting said alkylatable material with said alkylating agent in the presence of hydrofluoric acid, at least one of said alkylatable material and alkylating agent having had sufficient substantially dry steam admixed therewith to increase the dissolved $H_2O$ content of the hydrofluoric acid after said contacting to no more than about 5 wt. %, said contacting being at a temperature and pressure and for a contact time sufficient to alkylate said alkylatable material to produce high octane alkylate product.

12. The method of claim 11 wherein said substantially dry steam is superheated steam comprising at least about 25° F. of superheat.

13. The method of claim 11 wherein said steam-admixed hydrocarbon feed comprises entrained water, said method additionally comprising the step of decanting entrained water from said steam-admixed hydrocarbon feed prior to said contacting step.

14. The method of claim 13 wherein said decanting step comprises treating said steam-admixed hydrocarbon feed in a coalescing vessel wherein entrained water is separated from said steam-admixed hydrocarbon feed.

15. The method of claim 11 wherein said dissolved $H_2O$ content of the hydrofluoric acid after said contacting has been increased to no more than about 2 to 3 wt. %.

16. A method for the alkylation of a hydrocarbon feed, comprising contacting an alkylatable material comprising an isoparaffin comprising isobutane and an alkylating agent comprising at least one light olefin comprising at least one $C_3$–$C_5$ olefin, in the presence of hydrofluoric acid at HF alkylation conditions including temperature, pressure and contact time sufficient to alkylate said isoparaffin to produce a high octane alkylate product, said method involving addition of $H_2O$ wherein, absent the addition of $H_2O$, the hydrofluoric acid, after contact with hydrocarbon feed, has a dissolved liquid $H_2O$ content of less than about 1.5 wt. %, based on the combined weight of $H_2O$ and hydrofluoric acid, said method additionally comprising the steps of:

admixing sufficient superheated steam with said hydrocarbon feed to increase the dissolved $H_2O$ content of the hydrofluoric acid after contacting the hydrofluoric acid with the steam-admixed hydrocarbon feed to no more than about 2 to 3 wt. %, and decanting entrained water from said steam-admixed hydrocarbon feed, when entrained water is present therein resulting in the feed being substantially free of entrained water on contact with the hydrofluoric acid.

17. The method of claim 16 wherein said superheated steam comprises at least about 25° F. of superheat.

18. The method of claim 17 wherein said superheated steam comprises at least about 100° F. of superheat.

* * * * *